United States Patent [19]

Pahlck et al.

[11] Patent Number: 5,320,835
[45] Date of Patent: Jun. 14, 1994

[54] COSMETIC FORMULATION HAVING A PALETTE OF COLOR SHADES RENEWABLE BY MECHANICAL ACTION

[75] Inventors: Harold E. Pahlck, Waldwick, N.J.; Shari R. Martin, Suffern, N.Y.; Michael E. Squires, Mahwah, N.J.

[73] Assignee: Avon Products, Inc., Suffern, N.Y.

[21] Appl. No.: 935,646

[22] Filed: Aug. 26, 1992

Related U.S. Application Data

[63] Continuation of Ser. No. 798,274, Nov. 20, 1991, abandoned, which is a continuation of Ser. No. 634,932, Dec. 27, 1990, abandoned, which is a continuation of Ser. No. 443,262, Nov. 30, 1989, abandoned, which is a continuation-in-part of Ser. No. 426,204, Oct. 25, 1989, abandoned.

[51] Int. Cl.$^5$ ............................................. A61K 7/021
[52] U.S. Cl. ........................................ 424/64; 424/63
[58] Field of Search ................................... 424/63, 64

[56] References Cited

U.S. PATENT DOCUMENTS

| | | | |
|---|---|---|---|
| 3,947,571 | 3/1976 | Murphy et al. | 424/64 |
| 4,390,524 | 6/1983 | Nasuno et al. | 424/63 |
| 4,690,825 | 9/1987 | Won | 424/501 |
| 4,752,496 | 6/1988 | Fellows et al. | 427/27 |
| 4,756,906 | 7/1988 | Sweeny | 424/63 |
| 4,782,040 | 11/1988 | Revis et al. | 502/401 |
| 4,783,333 | 11/1988 | Mercado et al. | 424/63 |
| 4,839,163 | 6/1989 | Busch, Jr. | 424/63 |
| 4,873,091 | 10/1989 | Jankower et al. | 424/489 |
| 4,879,174 | 11/1989 | Marabella | 424/63 |
| 4,948,818 | 8/1990 | Carmody et al. | 521/149 |
| 4,950,634 | 8/1990 | Williams et al. | 502/401 |
| 4,950,635 | 8/1990 | Williams et al. | 502/401 |
| 5,126,381 | 6/1992 | Liscomb | 522/3 |
| 5,135,740 | 8/1992 | Katz et al. | 424/401 |

OTHER PUBLICATIONS

Technical Bulletin by Dow Corning (Form No. 24-55-0-88) entitled "Information About Specialty Copolymers".

"Polymer Development of Cosmetic Interest" by Eugene H. Gans, Ph.D. of Hastings Associates; published in vol. 103, Cosmetics and Toiletries, pp. 94-98.

Technical Bulletin by Dow Corning entitled "Polytrap: Methacrylate Polymeric Absorbents for Cosmetics and Toiletries".

*Primary Examiner*—Thurman K. Page
*Assistant Examiner*—James M. Spear
*Attorney, Agent, or Firm*—Hopgood, Calimafde

[57] ABSTRACT

Cosmetic formulations have activatable dormant pigments dispersed in an anhydrous base or vehicle. Shear forces applied to the cosmetic formulation following application to the skin causes activation of the dormant pigment thereby releasing the pigment and giving the original color of the anhydrous base or vehicle renewed intensity or a "long wearing" affect.

1 Claim, No Drawings

COSMETIC FORMULATION HAVING A PALETTE OF COLOR SHADES RENEWABLE BY MECHANICAL ACTION

This application is a continuation of application Ser. No. 07/798,274, filed Nov. 20, 1991, now abandoned, which is a continuation of application Ser. No. 07/634,932 filed, Dec. 27, 1990, now abandoned, which is a continuation of Ser. No. 07/443,262, filed Nov. 30, 1989, now abandoned, which is a continuation in part of application Ser. No. 07/426,204, filed Oct. 25, 1989, now abandoned.

TECHNICAL FIELD

The present invention relates generally to cosmetic preparations and more specifically, to novel pigmented compositions having "activatable" dormant colored particles or pigments dispersed throughout a cosmetic vehicle or base. The cosmetic vehicle or base may comprise lipstick, blush, face powder, foundation, eyeshadow or any other cosmetic preparation containing a colorant or pigment. In use, shear forces (e.g. rubbing onto the surface of the skin) activate the dormant color component causing a sustained release of pigment thereby giving the original color a renewed intensity or a "long wearing" affect. Alternatively, sustained release of the dormant pigment may lend an unusual but aesthetic look to the cosmetic base composition characterized by a juxtaposition of at least two or more different colors or by the creation of a new color comprising a blend of the original color and the released pigment.

BACKGROUND ART

U.S. Pat. No. 3,947,571 relates to the use of a microencapsulated oil in lipstick. Moisture applied to the lips after the lipstick has been applied results in a sustained release of oil from the capsules thus imparting a shiny "wet" look to the lips. This patent does not suggest microencapsulating pigment per se, nor does it suggest activating an encapsulated or dormant pigment by effecting rupture of the microcapsules via applied shear forces in order to achieve a "long wearing" affect.

U.S. Pat. No. 4,752,496 relates to the microencapsulation of "never dry" or paste cosmetics using the well known coacervation technique. After encapsulation the "greasy" cosmetic is applied to a substrate and subsequently overlaid with a film forming agent. The substrate may be used as samples capable of being distributed to consumers through the mail, or on inserts in magazines. Although this patent does suggest microencapsulating a "lipstick" formulation, it does not disclose nor suggest microencapsulation of a pigment in a cosmetic formulation (e.g. lipstick) for the purpose of rendering it dormant so that it subsequently may be activated to achieve a "long wearing" affect.

An Information Bulletin published by Dow Corning (Form No. 24-550-88) entitled "Information About Specialty Copolymers" describes a highly cross-linked polymethacrylate copolymer in the form of a fine particle-sized, freely flowing powder which may be used to absorb various liquid systems both volatile and non-volatile used in cosmetic formulations. The Information Bulletin states that the Dow Corning polymer, sold under the designation POLYTRAP Q5-6603, may be spread into a thin film on a surface, such as rubbing on the skin, to cause the absorbed fluids to come into contact with such surface. The Dow Corning Information Bulletin however, fails to suggest loading the polymethacrylate copolymer with a pigment so that the latter may be rendered dormant until "activated" or released on a sustained basis for renewing the color in a cosmetic formulation and achieving a "long wearing" affect.

Past attempts to provide acceptable cosmetic products having pigmented solid particles which may be activated or released on a sustained basis by the application of shear forces thereby giving a renewed color intensity or "long wearing" look have not been successful. When pigments were microencapsulated and placed directly into a cosmetic base, it was found that the microcapsules felt "gritty and hard" on the skin, thus rendering the composition unacceptable as a cosmetic product. Attempts to ameliorate this undesirable condition by mixing the solid particles with oils or emollients of various types to form a dispersion also resulted in failure by yielding microcapsules that were fragile, and thus too easily rupturable during handling, or pigment concentrations insufficient to give the desired renewed color intensity. When pigment was added to fine particle-size agglomerated powders combined with a cosmetic vehicle or base and then rubbed into the skin, intensification of color was inadequate to provide a "long wearing" affect.

These disadvantages were overcome by the present invention when it was discovered that in a first form cosmetically acceptable compositions may be produced having microencapsulated pigmented solid particles by forming a dispersion of the pigment in a hydrophobic, non-volatile, low viscosity liquid carrier; coacervating the dispersion to yield microcapsules in the form of a stable, freely flowing, dry powder; and then incorporating the microcapsules in a compatible anhydrous base or vehicle. In a second or alternatively preferred form of the invention, it was discovered that the pigment could be loaded onto a fine particle-size, high surface area, solid substrate and then coated with an adherring oil or outer film to entrap the pigment on the substrate. When the resulting cosmetic compositions were applied to the skin and rubbed or otherwise subjected to shear forces, the microcapsules and/or entrapping substrate particles were readily ruptured or otherwise mechanically distorted thereby releasing their intensely colored pigment and giving the compositions' color or shade a perceptible "long wearing" look.

DISCLOSURE OF THE INVENTION

Briefly described, the present invention contemplates cosmetic formulations having dispersed therein rupturable microcapsules the cores of which comprise pigmented solid particles dispersed in a hydrophobic, non-volatile, low-viscosity liquid carrier. The compositions are made by first forming the initial dispersion by mixing the pigmented solid particles with the liquid carrier, grinding the mixture to yield a uniform particle size distribution in the initial dispersion, and then microencapsulating the pigment/liquid carrier dispersion by coacervation to yield microcapsules in the form of a stable, free flowing, dry powder. The microcapsules then are further processed by being dispersed in a compatible cosmetic vehicle or base.

In an alternative embodiment, the pigment is applied to an entrapping substrate in the form of fine solid particles having a high surface area. The pigmented substrate is then coated with a film thereby yielding a stable, free flowing, dry powder which may be further processed by being dispersed in a compatible cosmetic vehicle or base.

BEST MODE FOR CARRYING OUT THE INVENTION

The present invention relates to cosmetic formulations useful for imparting color to the surface of the skin. Such formulations, generally referred to as "makeup", may have many different forms including without limitation lipstick, foundation, face powder, blush, eyeshadow and so on. Each makeup form, in turn, generally includes a color component in the form of pigmented solid particles for giving it its characteristic color or "shade", or other solid particles for giving it a desired texture or sheen (mica, pearlescents, waxes, etc.) with the color component being dispersed throughout a suitable anhydrous base or vehicle. For example, in the case of "lipstick" the coloring agent or pigmented ingredients may be dispersed in a base comprising a mixture of waxes, emollients, and moisturizers, whereas, in the case of "blush", the pigmented solids may be dispersed in a base comprising a mixture of talc, kaolin, and various known binders.

In whatever form, the color or shade of a particular applied makeup formulation usually fades with time as the pigmented solid particles are rubbed off or abraded during daily activity. It has long been a desirable objective in the cosmetic arts to render the original application of makeup color "long wearing" or renewable on a sustained basis without reapplication. In order to meet this objective of providing a cosmetic formulation having color renewable characteristics thereby giving it the desired "long wearing" look or quality, the present invention in a first preferred form contemplates dispersing the color component or pigmented solid in a liquid carrier, microencapsulating the liquid carrier dispersion to form a stable, dry, free flowing powder and then combining the resulting microcapsules with other compatible ingredients of a particular cosmetic base or vehicle.

In forming the initial dispersion, a selected colorant in the form of pigmented solid particles is mixed with a suitable liquid carrier in an amount ranging up to about 70% by weight of the total dispersion, i.e. the remainder of the dispersion comprises not less than about 30% by weight of the liquid carrier. As will be made more apparent below, this ratio may be adjusted however, depending upon the type of pigment selected and the type of liquid carrier selected, it being critical only that the viscosity of the resulting dispersion be less than about 4000 cps when measured at room temperature (78° F.).

An increase in the amount of pigment relative to the liquid carier generally will result in an increase in the viscosity of the dispersion leading to microcapsules that are too hard and gritty, whereas a decrease in pigment relative to the liquid may result in microcapsules that are too easily rupturable, or to less than desirable intensity of the released pigment or color. When utilizing a low viscosity liquid carrier (e.g. mineral oil) a pigment/liquid carrier ratio in the range of about 1:2 to about 1:1 has been found to achieve a good balance between color intensity, lack of "grittyness" and capsule integrity, and therefore, is mostly preferred.

Suitable pigments may comprise any organic or inorganic pigment or colorant approved for use in cosmetics by the CTFA and the FDA such as the lakes, iron oxides, titanium dioxide, iron sulfides, or other conventional pigments used in cosmetic formulations. Conventional approved dyes may also be used provided they are hydrophobic (water insoluble). The lakes (organic) and the iron oxides are particularly preferred because of their excellent color intensity.

The liquid carrier component of the initial dispersion must be inert, hydrophobic (water insoluble) and non-volatile, have a low viscosity and be capable of forming a colloidal suspension when the pigment granules are mixed therein. Any of the conventional oleophilic or oil compounds used in cosmetic formulations such as mineral oil, vegetable oil, peanut oil, lanolin oil, squalene, castor oil, isopropyl myristate, isopropyl palmirate, silicone oil, and diisopropyl dimerate, either alone or blended together, are suitable. However, because the viscosity of the initial dispersion prior to being microencapsulated must be carefully controlled within the desired range mentioned above, it has been found that a light or low viscosity mineral oil provides the best results. In this regard, a light mineral oil sold by Witco, Petrolla, Pa., under the designation "Carnation White Mineral Oil" is mostly preferred. Nonetheless, it will be appreciated that the other oil compounds mentioned above as well as those commonly used in the cosmetic arts may be employed instead so long as their viscosity is modified or controlled sufficiently to form a dispersion having a viscosity not more than about 4000 cps when measured at room temperature.

In accordance with the invention, the pigmented solid components and the liquid carrier are mixed together at room temperature in a conventional mixing kettle and then passed one or more times through a conventional grinding mill (e.g. a "stone" mill) until the resulting dispersion has a rich, creamy consistency with high gloss. Sufficient grinding of the dispersion will be achieved when a sample thereof measured on a standard Hegeman gauge reads no less than $6\frac{1}{2}$ indicating a maximum particle size of less than 20 microns. Since grinding of the pigment/liquid carrier phase in the grinding mill will tend to increase somewhat the viscosity of the dispersion; and furthermore, since the particle size of different pigments vary, it will be necessary to adjust the pigment/oil ratio up or down depending upon the different pigments employed for a given liquid carrier. This is illustrated in Table 1 below which shows the relative proportions of pigment and liquid carrier by percent weight which must be employed to achieve ground dispersions within the desired viscosity range comprising a range of different preferred pigments and the preferred liquid carrier (Carnation White Mineral Oil), respectively.

TABLE I

| | DISPERSION | | |
|---|---|---|---|
| PIGMENT | % PIGMENT | % CARRIER* | VISCOSITY(cps) 78° F. |
| D&C Red 7 Calcium Lake | 40 | 60 | 1550 |
| D&C Red 30 Talc Lake | 33 | 67 | 3500 |
| D&C Red 6 Barium Lake | 45 | 55 | 1800 |
| Russet Iron Oxide | 50 | 50 | 2200 |
| Yellow Iron Oxide | 40 | 60 | 2500 |
| Brown Iron Oxide | 50 | 50 | 2000 |

*Carnation White Mineral Oil

Whichever preferred pigment of Table 1 is utilized, it will be appreciated that the initial dispersion is characterized by a viscosity of less than about 4000 cps when measured at room temperature (78° F.), substantially uniform particle size distribution less than about 20 microns, and a substantially complete wetting of each particle by the liquid carrier (i.e. no agglomeration).

In accordance with the invention, the ground pigment/liquid carrier dispersion is microencapsulated to form stable, dry, free flowing powder of micro-sized particles whose diameter ranges from about 2 to about 20 microns. It has been found that microcapsules having a diameter larger than 20 microns results in an unacceptable cosmetic product by feeling rough or gritty on the skin.

The preferred method of microencapsulation is by the technique of coacervation. Under this method, which is well known and understood, a liquid dispersion is emulsified in a continuous, external aqueous phase to form micro-sized droplets and a complex of colloidal material added to the external phase is reacted upon in such a way to form a deposit on and around each droplet thereby forming an outer wall or shell. In the present case, the preferred colloids forming the outer wall or shell of each microcapsule comprise gelatin and gum arabic, the internal phase or core of which comprises the pigment/liquid carrier dispersion. After formation of the outer shells, the temperature of the aqueous coacervating solution is lowered causing gelation and hardening of the shell wall material. Further hardening may be accomplished by treating with a condensate polymer (e.g. urea formaldehyde) and applying a cross-linking agent (e.g. glutaraldehyde) to some or all of the available amino sites on the surface of the gelatin/gum arabic wall. Polymerization induced by the cross-linking agent causes the capsule's wall to harden sufficiently so that the microencapsules may be removed from the continuous external phase and dehydrated to form a stable, dry, free flowing powder capable of being handled easily and further processed to make cosmetic products without undue rupture of the microcapsules.

When the preferred coacervation method is used to form the microcapsules, the size of the cores, as well as the wall thickness and strength of the outer walls or shells, may be controlled precisely by altering such factors as the ph of the aqueous phase, the relative concentration of the colloids in the aqueous phase, the degree of agitation of the coacervation solution, the temperature and duration of the reaction, the degree of cross-linking, and so on, all as is fully known and understood in the art. Accordingly, these details form no part of and are outside the scope of the present invention. Suffice it to say, in practicing the invention, the initial pigment dispersion is microencapsulated to form capsules ranging in size from about 2 microns to about 20 microns, wherein the internal phase or core of pigment/oil preferably comprises from about 80% to about 90% of each capsule by weight; the outer shell components, i.e. gelatin and gum arabic, each comprises about 3% to about 5% by weight; the condensate polymer (urea formaldehyde) comprises about 4.00% to about 8.00% by weight; and the cross-linking agent (glutaraldehyde) comprises about 0.10% to about 0.50% by weight.

It has been found in accordance with the invention that microcapsules of the foregoing composition containing a core of pigment dispersed in a liquid carrier wherein the resulting dispersion has a viscosity of less than about 4000 cps when measured at room temperature are easily rupturable when subjected to shear forces (e.g. rubbing on the skin, eating, stroking of the cheeks, etc.), yet are capable of maintaining their integrity and withstanding rupture during the handling and processing steps necessary to form the novel cosmetic formulations contemplated herein.

The process of microencapsulation by coacervation is more fully described in the '496 Patent cited above, column 7, line 33 et seq., which patent and particularly the portion thereof describing "coacervation" being incorporated herein by this reference. The interested reader also is directed to U.S. Pat. Nos. 2,800,457, and 3,190,837, each of which further describes the details of the preferred coacervation microencapsulation technique, and each of which also is incorporated herein by this reference.

Following microencapsulation, the encased pigment/oil dispersion, now in the form of an easily handled, stable, dry free flowing powder is added to a compatible, anhydrous vehicle or base to form cosmetic products having a "long wearing" or renewable color characteristic. Owing to the relatively high concentration of pigment in each microcapsule core, a surprisingly small amount of microencapsulated pigment is necessary in each cosmetic vehicle to provide high intensity color renewability when the microcapsules are "activated", i.e. ruptured by being subjected to shear forces. In making a preferred form of "long wearing" lipstick, for example, about 5% of the lipstick base by weight may comprise microencapsulated pigment according to the invention. In a preferred formula for a "long wearing" powder blush, the microencapsulated pigment content may be about 10% of the vehicle by weight. Nonetheless, it will be understood that as much microencapsulated pigment may be added to a selected cosmetic vehicle or base as desired so long as the cosmetic form in question is still capable of being applied to the skin and the microcapsules do not feel granular or are otherwise apparent. In general, the particular preferred amount of microencapsulated pigment employed may range up to about 60% of the base vehicle with an amount in the range of about 2% to about 20% being mostly preferred. In use, light rubbing of the cosmetic preparation after application, or movement of the skin resulting from normal daily activities (e.g., smiling, pursing of the lips, eating, kissing, stroking of the cheeks) activates new color by causing rupture of the microcapsules and a release of pigment into the cosmetic base sufficient to produce a perceptible "long wearing" affect. The following Examples further illustrate the invention without limiting same wherein all quantities as stated are by weight percent.

EXAMPLE I

A pigmented oil dispersion in accordance with the invention was formulated as follows:

|  | | |
|---|---|---|
| | 40.00000% | D&C Red No. 7 Calcium Lake |
| | 60.00000% | Mineral Oil (Carnation White) |
| Total | 100.00000% | |

The following procedure was utilized. The pigment was added to the mineral oil in a Hobart Mixer and blended for 20 minutes at room temperature. The mixture was then passed through a Stone Mill twice (2X) and tested on a Hegeman gauge for particle fineness. The gauge reading was 6½ indicating that no pigment particle dispersed in the mineral oil was larger than 20 microns.

The consistency of the dispersion appeared rich and creamy with high gloss indicating a complete wetting of the pigment particles by the mineral oil with no agglomeration. The viscosity of the dispersion at room temperature measured 1550 cps on a Brookfield Model RVT viscometer.

EXAMPLE II

The dispersion or pigment grind of Example I was microencapsulated using a standard coacervation technique. The resulting microcapsules were less than 20 microns in diameter and were formulated as follows.

|   |   |
|---|---|
| 84.90000% | Pigment Dispersion (Example I) |
| 3.50000% | Gelatin |
| 4.00000% | Gum Arabic |
| 6.00000% | Urea Formaldehyde Polymer |
| 0.10000% | Glutaraldehyde |
| 1.50000% | Silica |
| Total 100.00000% | |

The microcapsules were in the form of a stable, dry, free flowing powder and although readily rupturable by light rubbing against the skin, they maintained their integrity during normal handling.

EXAMPLE III The microcapsules of Example II were added to a "lipstick" formulation as follows:

|   |   |
|---|---|
| 38.00000% | Castor Oil |
| 10.00000% | Diisopropyl Dimerate |
| 8.00000% | Isosteayl Neopentanoate |
| 5.00000% | Candelilla Wax |
| 3.50000% | Isopropyl Lanolate |
| 4.50000% | Lanolin |
| 3.50000% | Beeswax |
| 3.00000% | Microcrystalline Petroleum Wax |
| 3.00000% | PPG-5 Lanolin Wax |
| 2.00000% | Carnauba Wax |
| 1.50000% | Polybutene |
| 13.00000% | Colorants |
| 5.00000% | Encapsulated Pigment (Example II) |
| Total 100.00000% | |

The following process was utilized. A vessel was charged with the waxes (candelilla, beeswax, microcrystalline petroleum wax and carnauba) and brought up to 200° F. In a separate vessel the diisopropyl dimerate, isostearyl neopentanoate, lanolin, isopropyl lanolate, lanolin wax, and polybutene were added together and blended under medium speed conditions at a temperature of 175° F. When the waxes were at 200° F. in the first vessel they were added to the second vessel under conditions of medium speed mixing. The colorants were ground in the castor oil in a three-roll mill to a fineness of 6½ or greater on the Hegeman gauge and added to the second vessel and mixing was continued until the colorants were completely dispersed. The temperature of the second vessel was reduced to 170° F. followed by the addition of the microencapsulated pigment while medium speed mixing was continued until the microcapsules were completely dispersed. The mixture was then removed from the second vessel, poured into molds, passed through a cooling tunnel maintained at a temperature in the range of 35°–42° F., extracted from their molds, and flamed to produce lipsticks. A lipstick from the batch was applied to the lips of a subject and shear forces applied via normal activity, i.e. pursing of the lips, eating, drinking, smiling, and talking. The shear forces induced by such activity to the lip region caused a quantity of the microcapsules to rupture, thereby releasing additional color on the lips. As a result, color intensity remained for a longer duration compared to lipsticks that did not contain the microencapsulated pigment.

EXAMPLE IV

The following formulation was used to make "blush" utilizing the microencapsulated pigment of Example II.

|   |   |
|---|---|
| 23.00000% | Mica |
| 22.00000% | Talc |
| 9.00000% | Neopentaglycol Dicapryl Dicaprate |
| 9.00000% | Bismuth Oxychloride |
| 4.00000% | Calcium Stearate |
| 1.50000% | Calcium Silicate |
| 1.50000% | Synthetic Wax (and) Corn Gluten Protein |
| 0.60000% | Wool Wax Alcohols |
| 0.25000% | D&C Red 7 Calcium Lake |
| 3.75000% | D&C Red 6 Barium Lake |
| 0.19000% | Iron Oxide Red |
| 0.04000% | Iron Oxide Yellow |
| 0.13000% | D&C Red 6 Barium Lake |
| 10.04000% | Timiron MP-1001 |
| 15.00000% | Microencapsulated Pigment (Example II) |
| Total 100.00000% | |

The "blush" was made in accordance with the following procedure. The talc, colorants, calcium stearate, calcium silicate and bismuth oxychloride were added to a mixing vessel and blended together under high speed conditions to thoroughly intermix the ingredients at room temperature. The mixing vessel consisted of 24 liter NOVA Model Baker-Perkins disperser/granulator having a 12-inch impeller driven at 360 rpm and a high speed granulator blade driven at 3000 rpm. The ingredients were removed from the mixing vessel and pulverized in a MIKROPUL micropulverizer to reduce the particle size of the ingredients to less than about 10 microns. The pulverized ingredients were returned to the main mixing vessel and mica was added under high speed blending conditions. The wool wax alcohols and neopentaglycol dicapryl dicaprate were mixed together in a separate jacketed kettle and the temperature was increased to 175° F. The heated mixture was sprayed under a pressure of 50 psi into the main mixing vessel while high speed mixing continued. The blended ingredients were removed from the main kettle and pulverized once again to insure a thorough dispersion of the oils in the particulate ingredients. The pulverized ingredients were returned to the main mixing vessel and the microencapsulated pigments added under continuous high speed mixing until evenly dispersed throughout the blend. The intermixed ingredients were removed and compressed into a shallow pan on an ALITE powder press. The blush was applied from the pan via a brush applicator to the cheeks of a subject. As a result of normal daily activity e.g. smiling, eating, talking and stroking the cheeks, a quantity of microcapsules were ruptured thereby releasing additional color to the cheeks. The additional color provided more intense color and a perceived long lasting affect compared to blush made in accordance with the same formulation, but not containing any microencapsulated pigment.

EXAMPLE V

A pigmented oil dispersion in accordance with the invention was formulated as follows:

| | | |
|---|---|---|
| | 50.00000% | Russet Iron Oxide |
| | 50.00000% | Mineral Oil (Carnation White) |
| Total | 100.00000% | |

The following procedure was employed. The pigment was added to the mineral oil in a HOBART Mixer and blended for 20 minutes at room temperature. The mixture was then passed through a stone mill twice (2X) and tested on a Hegeman gauge for particle fineness. The gauge reading was 6½ indicating that no pigment particle dispersed in the mineral oil was larger than 20 microns. The consistency of the dispersion appeared rich and creamy, with high gloss indicating a complete wetting of the pigment particles by the mineral oil with no agglomeration. The viscosity of the dispersion at room temperature measured 2200 cps on a Brookfield Model RVT viscometer.

EXAMPLE VI

The dispersion or pigment grind of Example V was microencapsulated using a standard coacervation technique. The resulting microcapsules were less than 20 microns in diameter and were formulated as follows:

| | | |
|---|---|---|
| | 84.90000% | Pigment dispersion (Example V) |
| | 3.50000% | Gelatin |
| | 4.00000% | Gum Arabic |
| | 6.00000% | Urea Formaldeyde Polymer |
| | 1.50000% | Silica |
| | 0.10000% | Glutaraldehyde |
| Total | 100.00000% | |

EXAMPLE VII

The following formulation was used to make "eyeshadow" utilizing the microencapsulated pigment of Example VI.

| | | |
|---|---|---|
| | 2.75000% | Mica |
| | 5.00000% | Zinc Stearate |
| | 1.50000% | Silica |
| | 10.00000% | Synthetic Wax (and) Corn Gluten Protein |
| | 1.02000% | Black Iron Oxide |
| | 0.50000% | Cosmetic Red Iron Oxide |
| | 0.68000% | Chromium Hydrate Green |
| | 20.40000% | Timica Brillant Gold |
| | 29.75000% | Timica Silk White |
| | 3.40000% | Timiron Super Gold |
| | 10.00000% | Decyl Oleate |
| | 15.00000% | Microencapsulated Pigment (Example VI) |
| Total | 100.00000% | |

The "eyeshadow" was made in accordance with the following procedure. The colorants, zinc stearate and silica were added to a mixing vessel and blended together under high speed conditions to thoroughly intermix the ingredients at room temperature. The mixing vessel consisted of a 24 liter NOVA model BAKER-PERKINS disperser/granulator having a 12-inch impeller driven at 360 rpm and a high speed granulator blade driven at 3000 rpm. The ingredients were removed from the mixing vessel and pulverized in a MIKROPUL micropulverizer to reduce the particle size of the ingredients to less than about 10 microns. The pulverized ingredients were returned to the main mixing vessel and mica was added under high speed blending conditions. The decyl oleate, synthetic wax and corn gluten protein were placed in a separate jacketed mixing kettle and the temperature increased to 175° F. The heated oil/wax mixture then was sprayed under a pressure of 50 psi into the main mixing vessel while high speed blending continued for two minutes to disperse the oil wax throughout the powdered ingredients. The blend was removed from the main mixing vessel and pulverized once again to assure a thorough dispersion of the oils in the particulate ingredients. The pulverized, dispersed ingredients were then returned to the main mixing vessel and the microencapsulated pigment added under continuous high speed blending to disperse the microencapsulated pigments throughout the blend. The blend was removed and compressed into a shallow pan on an Alite Powder Press. The eyeshadow in the pan, which had a beige color, was applied via a brush to the eyelids of a subject. After rubbing with a sponge tipped applicator to induce rupture of a quantity of microcapsules, the original beige color changed to a deep bronze color and the intensity of the new color appeared to be greater than the original color.

EXAMPLE VIII

A lipstick was made in accordance with the following formulation utilizing the process described above in connection with Example III.

| | | |
|---|---|---|
| | 43.00000% | Castor Oil |
| | 10.00000% | Diisopropyl Dimerate |
| | 8.00000% | Isostearyl Neopentanoate |
| | 5.00000% | Candelilla Wax |
| | 4.50000% | Lanolin |
| | 3.50000% | Isopropyl Lanolate |
| | 3.50000% | Beeswax |
| | 3.00000% | Microcystalline Petroleum Wax |
| | 3.00000% | PPG-5 Lanolin Wax |
| | 2.00000% | Carnauba Wax |
| | 1.50000% | Polybutene |
| | 13.00000% | Colorants |
| Total | 100.00000% | |

The lipstick material was melted down in a jacketed kettle and microencapsulated using a standard coacervation technique. The resulting microcapsules were added to the above lipstick formula at 10 percent by weight and an equivalent amount of castor oil was removed. The procedure of Example III was again followed to make lipstick having the 10 percent encapsulated lipstick ingredient therein. A sample of the resulting lipstick was applied to the lips of a subject and normal activity simulated. Although a certain amount of capsules were ruptured and additional color was released on the lips, the color intensity was too low to give any perceived long wearing affect. Moreover, an unpleasant, rough feeling was perceived upon application, and the encapsulated material left an unpleasant gritty residue on the lips. In view of these factors, the formulation of this Example was considered not to be an acceptable cosmetic product.

The foregoing Examples illustrate how in accordance with the present invention microencapsulation is effective to render the activatable pigment dormant in the host cosmetic formulation. Nonetheless, other means suitable for making the pigment dormant and activatable by shear forces may be employed instead without departing from the principles of the invention. Thus, in an alternatively preferred embodiment of the invention, it has been found that the pigment to be released on a sustained basis may be rendered activatable by entrappment on or within a sol id substrate combined with the cosmetic vehicle or base in question. The preferred entrapping medium comprises a fine particle-sized, solid particulate that is inert, hydrophobic, and insoluble and which contains many pores or sites giving it a high surface area per unit volume. In general, any particulate approved for use in cosmetics and meeting the foregoing criteria is suitable. Examples include polymethacrylate copolymers, silica beads, and porous nylon powders with the polymethacrylate copolymer sold by Dow Corning under the designation POLYTRAP Q5-6603 being mostly preferred. The mostly preferred entrapping medium consists of micro-sized particles of copolymer pressed together to form agglomerates (20–80 microns) which, in turn, are loosely clustered into aggregates of 200 to 1200 microns in size. The copolymer is available in the form of a stable, dry free flowing powder facilitating its use in cosmetic formulations.

Any of the pigments or dyes mentioned above may be loaded onto the polymethacrylate copolymer agglomerates by mixing the colorants with the copolymer powder in a suitable blender such as a Baker-Perkins disperser/granulator. In general, 1 to 2 parts pigment per part of copolymer are mixed together. It is believed that the pigment mechanically attaches to the irregular copolymer surface and lodges in the nooks and crannies thereof rather than be absorbed as in the case of liquid systems being loaded onto the copolymer. In order to maintain the pigment or colorant stable on the copolymer, in accordance with the invention, a thin film or layer is applied to the pigment loaded copolymer subtrate. Generally, any non-volatile, oleophilic liquid approved for use in cosmetics is suitable for this purpose such as the oil compounds mentioned above in connection with the first preferred form of the invention with the light (low viscosity) mineral oil such as the "Carnation White" form available from Witco being mostly preferred. The amount of liquid adherent is not critical so long as a sufficient amount is present to completely wet the pigment particles on the copolymer surface with due allowance being given for the high absorbtion capability of the particulate. Generally from 0.2 to 1.4 parts of liquid adherent to 1 part pigment is suitable. Based upon the copolymer content the liquid adherent should range from about 0.25 to 1.0 parts for each part of the copolymer. The liquid adherent may be added to the pigment/copolymer blend in a standard mixer and blended thoroughly to disperse the liquid throughout the solids. If desired, suitable processing aids such as fumed silica may be added to the pigment before the liquid is added. After mixing these ingredients together, the pigment entrapped copolymer will be in the form of a stable, dry, free flowing powder.

The pigment entrapping powder may then be added to a conventional, compatible, anhydrous cosmetic base or vehicle as in the first embodiment to produce cosmetic formulations containing "activatable" dormant pigment suitable when activated or released to give the formulation a "long wearing" affect regarding its color or shade. In use, a slight rubbing of the cosmetic formula into the skin will tend to rupture or otherwise mechanically distort the aggregated polymethacrylate copolymer material thereby releasing and spreading the pigment/liquid adherent dispersion on the surface of the skin, thus activating the colorant and giving the formulation its "long wearing" or renewed color characteristic. The same results may be achieved by applying other shear forces, say, in the case of lipstick, for example, those occassioned by eating, pursing of the lips, kissing, smiling, and so on.

The foregoing alternatively preferred form of the invention will now be further illustrated by the following Examples which are not to be construed as limiting and wherein all stated quantities are by percent weight.

EXAMPLE IX

A stable, dry, free flowing powder comprising a pigment loaded substrate was prepared having the following formulation:

| | | |
|---|---|---|
| | 29.00000% | D&C Red 7 Calcium Lake |
| | 1.00000% | Silica-Fumed |
| | 40.00000% | Polymethacrylate* |
| | 30.00000% | Mineral Oil (Carnation White) |
| Total | 100.00000% | |

*Dow Corning POLYTRAP Q5-6603

The following procedure was utilized. The pigment and silica-fumed were blended together in a 24 liter NOVA model BAKER-PERKINS disperser/granulator under high speed conditions for three minutes. This mixture was then micropulverized to a particle size than about 10.0 microns using a MIKROPUL micropulverizer. The pulverized blend was returned to the mixing vessel and aggregates of polymethacrylate (800 to 1200 microns) were added while high speed blending continued for an additional one minute to break down the aggregates and evenly disperse the pigment throughout the mixture. The mineral oil was then sprayed into the mixing vessel at room temperature under 50 psi pressure while high speed blending continued for an additional one minute to thoroughly coat and wet the pigment and polymethacrylate blend. The mixture was then passed through the MIKROPUL micropulverizer to further assure that the oil was thoroughly adsorbed onto the surface of the substrate material thereby entrapping the pigment thereon. The final mixture was in the form of a pigmented, stable, dry, free flowing powder.

EXAMPLE X

A "lipstick" was made in accordance with Example III, but for the substitution of the entrapped, pigmented powder of Example IX in lieu of the encapsulated pigment powder, i.e. the entrapped, pigmented powder (Example IX) comprised 5% by weight of the lipstick formulation of Example III. The lipstick was formulated following the procedure of Example III. A lipstick from the batch was applied to the lips of a subject and shear forces applied via normal activity, i.e. pursing of the lips, eating, drinking, smiling and talking. The shear forces induced by such activity to the lip region caused a quantity of the entrapped pigment to be released, thereby providing additional color. As a result, the color intensity remained for a longer duration compared to lipsticks that did not contain the entrapped pigment blend.

EXAMPLE XI

A powder "blush" was made in accordance with Example IV, but for the substitution of the entrapped, pigmented powder of Example IX in lieu of the encapsulated pigment powder, i.e. the entrapped, pigmented powder (Example IX) comprised 15% by weight of the blush formulation of Example IV. The same procedure as in Example IV was followed. The blush was applied from the pan via a brush applicator to the cheeks of a subject. As a result of normal daily activity, e.g. smiling, eating, talking and stroking the cheeks, a quantity of the entrapped pigment was released, thereby, providing additional color. The newly released pigment provided more intense color and a perceived longer lasting affect compared to blush made in accordance with the same formulation, but not containing the entrapped pigment.

EXAMPLE XII

A stable, dry, free flowing powder comprising a pigment loaded substrate was prepared having the following formulation:

|   |   |
|---|---|
| 29.00000% | Russet Iron Oxide |
| 1.00000% | Silica-fumed |
| 40.00000% | Polymethacrylate* |
| 30.00000% | Mineral Oil (Carnation White) |
| Total 100.00000% | |

*Dow Corning POLYTRAP Q5-6603

The procedure of Example IX was utilized.

EXAMPLE XIII

A powder "eyeshadow" was made in accordance with Example VII, but for the substitution of the entrapped, pigmented powder of Example XII in lieu of the encapsulated pigment powder, i.e. the entrapped, pigmented powder (Example XII) comprised 15% by weight of the eyeshadow formulation of Example VII. The same procedure as Example VII was followed. The eyeshadow in the pan, which had a beige color, was applied via a brush applicator to the eyelids of a subject. After rubbing with a sponge tipped applicator to induce release of the entrapped pigment, the original beige color changed to a deep bronze color and the intensity of the new color appeared to be greater than the original color.

EXAMPLE XIV

A stable, dry, free flowing powder comprising a pigment loaded substrate was prepared having the following formulation:

|   |   |
|---|---|
| 37.31000% | D&C Red #7 Ca Lake |
| 1.50000% | Silica-fumed |
| 37.31000% | Lecithin Treated Silica Beads |
| 23.88000% | Mineral Oil (Carnation White) |
| Total 100.00000% | |

The procedure of Example IX was utilized, but for the substitution of micron-sized lecithin treated silica beads for the aggregates of polymethacrylate. The silica beads were obtained from U.S. Cosmetics Corp., Putnam, Conn.

EXAMPLE XV

A powder "blush" was made in accordance with Example IV, but for the substitution of the entrapped, pigmented powder of Example XIV in lieu of the encapsulated pigment powder, i.e. the entrapped, pigmented powder (Example XIV) comprised 15% by weight of the blush formulation of Example IV. The blush was applied from the pan via a brush applicator to the cheeks of a subject. As a result of normal daily activity, e.g. smiling, eating, talking and stroking the cheeks, a quantity of the entrapped pigment was released, thereby, providing additional color. The newly released pigment provided more intense color and a perceived longer lasting affect compared to blush made in accordance with the same formulation, but not containing the entrapped pigment.

EXAMPLE XVI

A stable, dry, free flowing powder comprising a pigment loaded substrate was prepared having the following formulation:

|   |   |
|---|---|
| 43.95000% | D&C Red #7 Ca Lake |
| 1.10000% | Silica-fumed |
| 44.00000% | Porous Nylon Powder |
| 11.00000% | Mineral Oil (Carnation White) |
| Total 100.00000% | |

The procedure of Example IX was utilized, but for the substitution of poreus nylon powder for the aggregates of polymethacryl ate. The nylon powder (99% passing through a 400 mesh (38 micron) screen) was obtained from the Torey Company, New York, N.Y.

EXAMPLE XVII

A powder "blush" was made in accordance with Example IV, but for the substitution of the pigment entrapped powder, of Example XVI in lieu of the encapsulated pigment powder, i.e. the pigment entrapped powder, (Example XVI) comprised 15% by weight of the blush formulation of Example IV. The blush was applied from the pan via a brush applicator to the cheeks of a subject. As a result of normal daily activity, e.g. smiling, eating, talking and stroking the cheeks, a quantity of the entrapped pigment was released, thereby, providing additional color. The newly released pigment provided more intense color and a perceived longer lasting affect compared to blush made in accordance with the same formulation, but not containing the entrapped pigment.

In carrying out the present invention it will be appreciated that combinations of the alternatively preferred forms as described above may be employed in a single cosmetic vehicle or base. Thus, where it is desired to achieve a dormant pigment palette comprising both intense and subtle colors in the same vehicle, the encapsulated pigment of the first form of the invention (which provides an intense burst of color when activated) may be mixed with the entrapped substrate of the second form (which provides a more gradual shading of color when activated) in the same vehicle employing the relative proportions necessary to obtain the precise effect or palette sought. This yet further preferred form of the invention will now be illustrated by the following Example which is not to be construed as limiting and wherein all stated quantities are in percent weight.

EXAMPLE XVIII

The encapsulated pigment of Example II was combined with the pigment entrapped substrate of Example XI to form a powder "blush" having the following formulation:

|   |   |
|---|---|
| 30.00000% | Mica |
| 22.00000% | Talc |
| 9.00000% | Neopentaglycol Dicapryl Dicaprate |
| 9.00000% | Bismuth Oxychloride |

| | |
|---:|---|
| 4.00000% | Calcium Stearate |
| 1.50000% | Calcium Silicate |
| 1.50000% | Synthetic Wax (and) Corn Gluten Protein |
| 0.60000% | Wool Wax Alcohols |
| 0.25000% | D&C Red 7 Calcium Lake |
| 3.75000% | D&C Red 6 Barium Lake |
| 0.19000% | Iron Oxide Red |
| 0.04000% | Iron Oxide Yellow |
| 0.13000% | D&C Red 6 Barium Lake |
| 10.04000% | Timiron MP-1001 |
| 3.00000% | Microencapsulated Pigment (Example II) |
| 5.00000% | Entrapped Pigment (Example IX) |
| Total 100.00000% | |

The powder "blush" was made utilizing the procedure of Example IV. The blush was applied from the pan via a brush applicator to the cheeks of a subject. As a result of normal daily activity e.g. smiling, eating, talking and stroking the cheeks, a quantity of the microcapsules and/or entrapped pigments were ruptured thereby releasing additional color to the cheeks. The additional color provided more intense color and a perceived long lasting affect compared to the blush made in accordance with the same formulation, but not containing any microencapsulated and/or entrapped pigment. Moreover, the resulting palette of renewable color comprised two components, i.e. an intense component and a more subtley shaded component.

It is evident from the foregoing that the present invention in its broadest sense contemplates the provision of an activatable dormant pigment in a cosmetic formulation wherein activation of the dormant pigment by applied shear forces releases color into the formulation thereby renewing the original color of the formulation with the same or a different shade and giving the formulation a "long-wearing" affect with regard to color. By encapsulating the pigment or entrapping it on a substrate as disclosed hereinabove the pigment is rendered inactive or dormant until the application of shear forces. Thus, the term "activatable" as used in the specification and claims means the release of the pigment from its dormant state in the cosmetic formulation to an active state where it renews, reinforces, or enhances the intensity of the original color, or it juxtaposes a new or different color relative to the original color thereby producing striking and aesthetic effects.

Although different forms of the present invention have been fully described above with reference to actual Examples thereof, this was done merely for the sake of illustrating preferred embodiments of the invention as required by statute. Obviously, many changes, modifications, and alterations may be made without departing from the principles of the invention. Accordingly, it is desired that the present invention be limited only by the true spirit and scope of the annexed claims.

We claim:

1. A cosmetic formulation having a renewable palette of color shades comprising:

a base phase characterized by a color;

a quantity of microcapsules dispersed in said base phase, said microcapsules each containing a colorant which is released into the base phase when said microcapsules are fractured by mechanical action applied to said cosmetic formulation to produce an intense shade in the color which characterizes said base phase, said microcapsules each having a diameter in the range of about 2 to about 20 microns; and a quantity of colorant entrapping substrate particles dispersed in said base phase, said colorant entrapping substrate particles each having an irregular surface for entrapping said colorant which is released into said base phase when mechanical action is applied to said cosmetic formulation to produce a subtle shade in the color which characterizes said base phase, said colorant entrapping substrate particles forming agglomerates of about 20 to about 80 microns, said agglomerates further forming aggregates in the range of about 200 to about 1200 microns, whereby the combined effect of said intense shade and said subtle shade produces a palette of color shades in said base phase which is renewable by mechanical action applied to said cosmetic formulation.

* * * * *